United States Patent

Lai et al.

Patent Number: 6,074,411
Date of Patent: Jun. 13, 2000

[54] MULTIPLE DIODE LASER APPARATUS AND METHOD FOR LASER ACUPUNCTURE THERAPY

[76] Inventors: Ming Lai; Meijuan Yuan, both of 2705 Avenida De Anita, #31, Carlsbad, Calif. 92008

[21] Appl. No.: 09/055,420

[22] Filed: Apr. 4, 1998

[51] Int. Cl.[7] .................................................. A61N 5/00
[52] U.S. Cl. .............................................. 607/89; 607/90
[58] Field of Search ...................... 607/3, 45–48, 607/88, 89, 90; 600/26, 27; 604/116; 606/2, 10, 13, 17

[56] References Cited

U.S. PATENT DOCUMENTS

| | | |
|---|---|---|
| D. 363,129 | 10/1995 | Landers et al. . |
| 4,232,678 | 11/1980 | Skovajsa . |
| 4,895,149 | 1/1990 | Morez ........................ 607/88 |
| 5,522,813 | 6/1996 | Trelles ....................... 607/89 |
| 5,643,173 | 7/1997 | Welles ....................... 607/88 |
| 5,755,752 | 5/1998 | Segal ......................... 608/89 |
| 5,879,373 | 3/1999 | Roper et al. ............... 600/322 |

OTHER PUBLICATIONS

Product Specification of He–Ne Physiotherapeutic Lasers.

*Primary Examiner*—Linda C. M. Dvorak
*Assistant Examiner*—Bryan K. Yarnell

[57] ABSTRACT

A laser apparatus and method is described for laser acupuncture therapy. A plurality of diode laser modules, a self-adhesive holder for each of the modules, and a timer-controlled power supply are implemented.

13 Claims, 4 Drawing Sheets

MULTIPLE DIODE LASER APPARATUS AND METHOD FOR LASER ACUPUNCTURE THERAPY

FIELD OF THE INVENTION

The present invention relates to a laser device. In particular, the present invention relates to a laser device for acupuncture therapy.

BACKGROUND OF THE INVENTION

Laser acupuncture therapy has been used as an alternative or complementary treatment of traditional acupuncture therapy. In a laser acupuncture therapy, a low power laser beam is used to replace a needle to stimulate an acupuncture point on a patient's body. It has proven effectiveness in many treatments and is less painful comparing to traditional needle treatment.

Various laser devices have bean developed and used for acupuncture treatment based on such lasers as He—Ne or diode lasers. These laser acupuncture devices implement one or two laser output channels delivered from a hand-held applicator. One design of the hand-held applicator is described by Landers et al. in U.S. Pat. No. D363,129.

To use these devices, a therapist needs to hold the applicator steadily to point the laser beam onto an acupuncture point. In an acupuncture treatment, stimulating five to ten acupuncture points are common and each point takes typically five to thirty minutes. Thus, a therapist needs to point the laser beam to one acupuncture point then another for a long time. Obviously, using these devices is inconvenient and is time consuming.

SUMMARY OF THE INVENTION

A primary objective of the present invention is to make a user friendly device for laser acupuncture therapy. The present invention is embodied in a laser device having a plurality of diode laser modules, a self-adhesive holder for each of the modules to be attach onto a patient's body, and a timer-controlled controller to power all the modules.

Each of the diode laser modules houses a diode laser to produce a laser beam at a selected wavelength. The diode laser module is preferably compact and light.

The self-adhesive holder is attachable to the diode laser module and is configured to hold the diode laser module. It has an adhesive surface and allows to attach a diode laser module onto an acupuncture point of a body part free of hand holding.

The controller is electrically connected to the diode laser modules and configured to provide electrical power to the diode lasers and to modulate the output power of the laser beams. A timer controlled switch is further implemented into the power supply controller for automatically controlling the duration of the treatments.

A laser device in accordance with the present invention thus enables a therapist to stimulate many acupuncture points simultaneously and to treat several patients at the same time. These and other aspects and advantages of the invention will become more apparent in the following drawings, detailed description and claims.

DETAILED DESCRIPTION OF THE PREFERRED EMBODIMENTS

Figure 1:
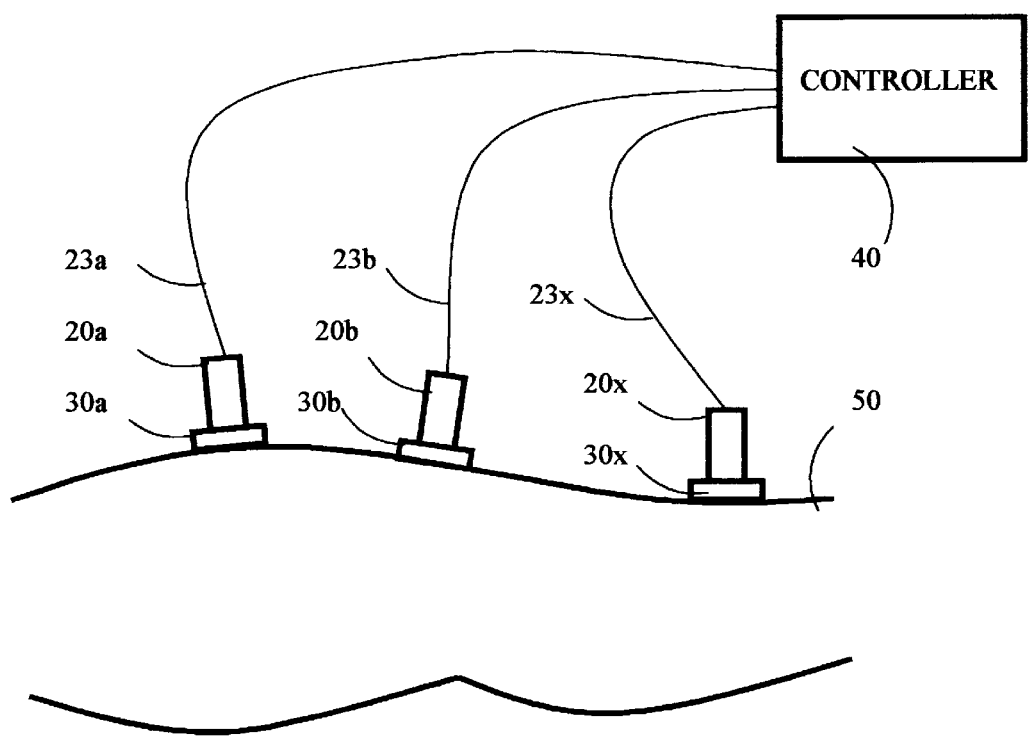
FIG. 1 is a schematic diagram of one embodiment of the present invention.

FIG. 1 shows a schematic diagram of a laser device 10 according to one embodiment of the present invention. A plurality of diode laser modules 20a through 20x is attached onto a patient's body part 50 by a set of self-adhesive holders 30a through 30x. Any number of diode laser modules may be used. Five to ten modules are preferred to treat multiple acupuncture points at the same time. Each diode laser module (e.g., 20a, 20b, and 20x) is connected electrically to a controller 40 by an electrical link (e.g., 23a, 23b, and 23x). The controller 40 provides electrical power to the diode laser modules and modulates the output power of each diode laser. The controller 40 may include a timer to automatically switch on or off the power to the diode laser modules.

In operation, a therapy laser beam produced by a diode laser module (e.g., 20a) is pointed directly at an acupuncture point. The laser power can be automatically modulated by the controller 40 to meet different requirements for a variety of laser acupuncture treatments. The self-adhesive holder (e.g., 30a) is configured to securely hold the diode laser module and to maintain the laser beam at the acupuncture point. Such holding mechanism is particularly advantageous since it eliminates the need for hand holding the laser module and allows the therapist to perform other tasks.

Figure 2:
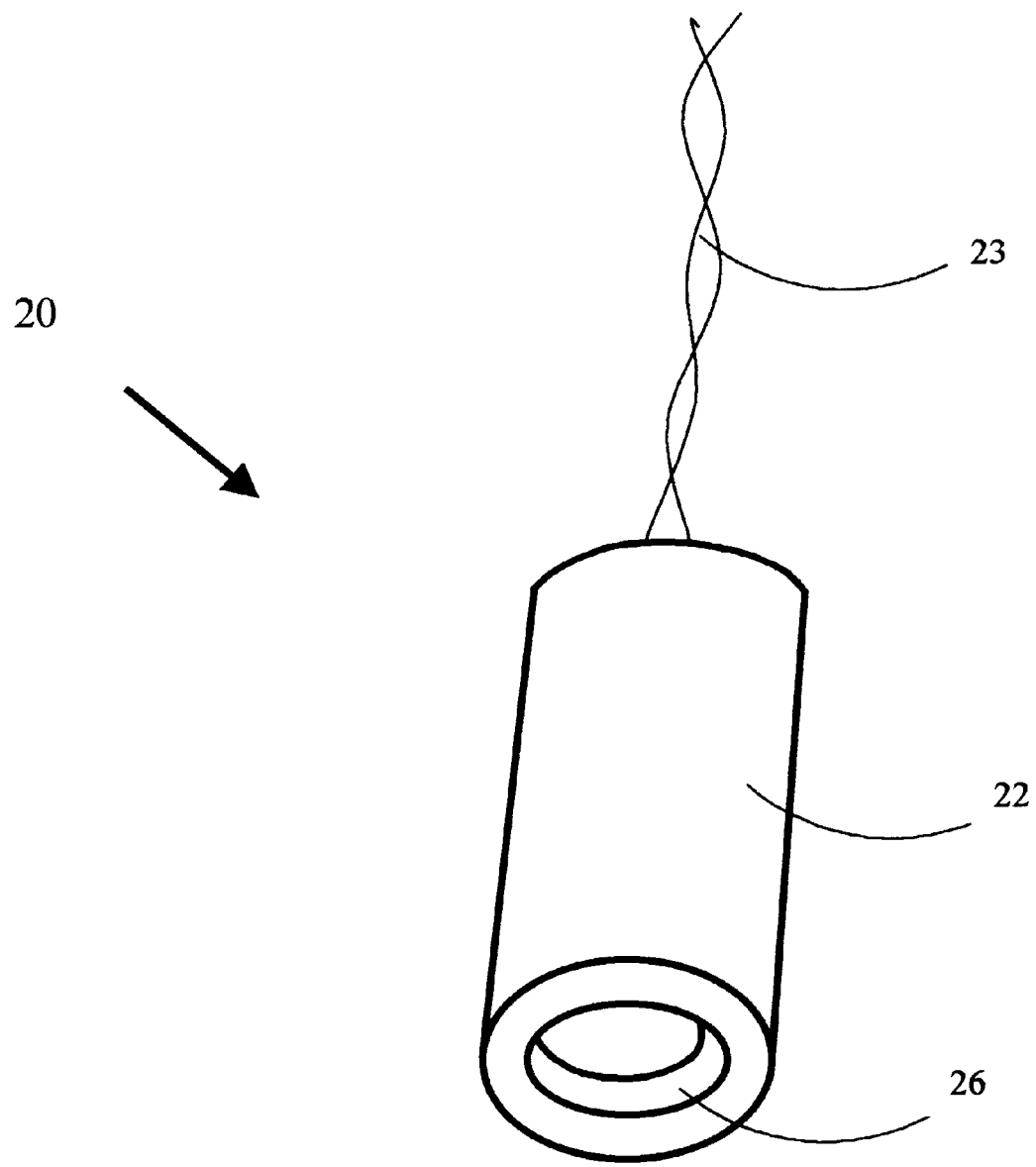
FIG. 2 is a schematic diagram showing one embodiment of a diode laser module.

FIG. 2 depicts one embodiment 20 of a diode laser module. The diode laser module 20 has a case 22 for housing a diode laser and its focusing optics, which are not shown in the drawing. The output laser beam exits the diode laser module 20 from the aperture 26 and is directed along the axis of the case 22. An electrical link 23, which may include one or more wires, connects the diode laser to the controller 40 as shown in FIG. 1. Preferably, each wire is thin and flexible. A driving circuit of the diode laser can be installed either inside the case 22 or inside the controller 40.

The output laser power from the diode laser module 20 should be about 5 mW, while a range of 1 mW to 100 mW may be used. The emitting wavelength of the diode laser module 20 is selected to have a desirable penetration depth for effectively stimulating an acupuncture point. For example, the laser wavelength may be at or around 635 nm to match the He—Ne laser or near 830 nm to increase the laser penetration depth. Any wavelength ranged from 500 nm to 1500 nm may be chosen for a variety of laser acupuncture treatments.

The diode laser module 20 is preferably compact and light. Commercial diode laser modules are available with approximately 1 cm in diameter, 2.5 cm in length, and a weight of 5 grams. Such laser modules can be used to implement the present invention.

Figure 3:
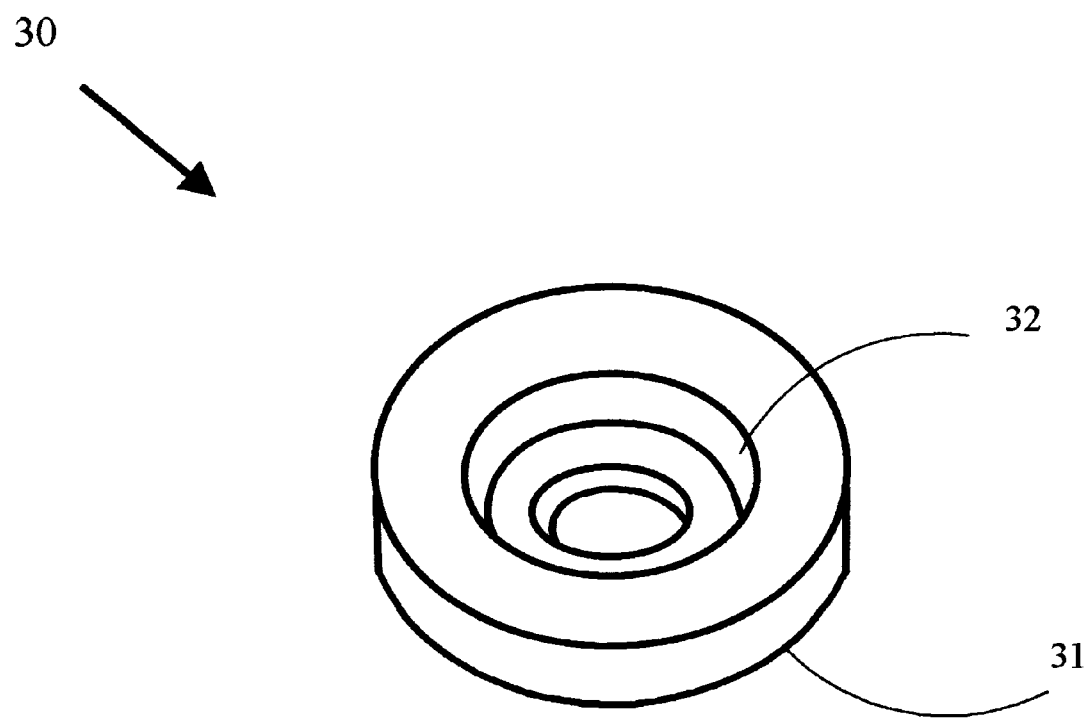
FIG. 3 is a schematic diagram showing a self-adhesive holder.

FIG. 3 shows one embodiment 30 of a self-adhesive holder for attaching a diode laser module onto a patient's body. The holder 30 has a first end shaped to engage to the end of the case 22 and a second end having a self-adhesive surface 31 for sticking onto a body part 50. The first end may have a counterbored hole 32 into which a diode laser module can inserted and held. Preferably, the holder 32 is configured to prevent the diode laser module 20 from contacting the body part 50.

The holder 30 is preferably made of a flexible material with a low thermal conductivity, including but not limited to soft plastic, foam paper, etc. In addition, the holder 30 may be a disposable item.

Figure 4:
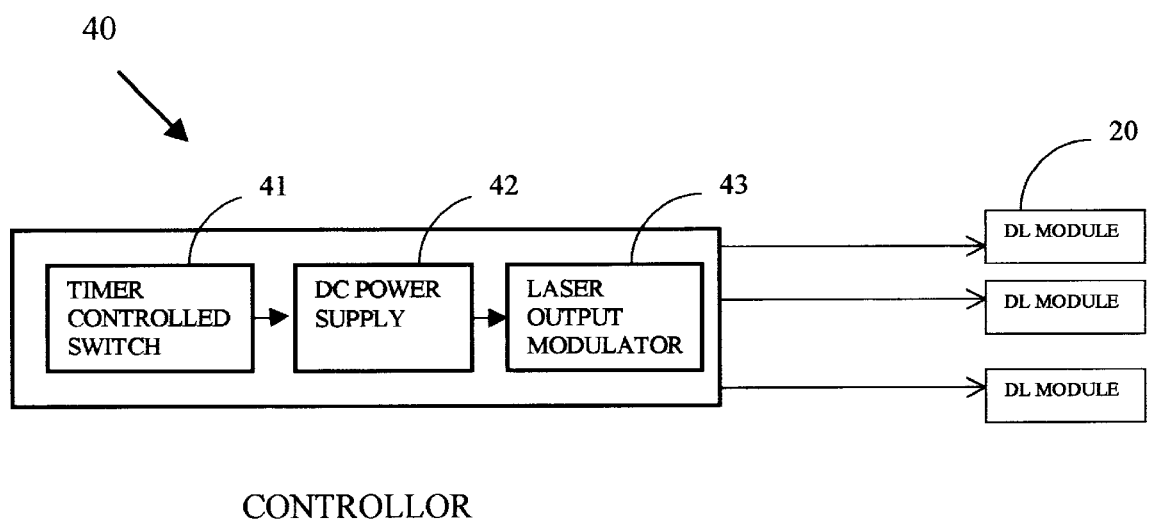
FIG. 4 is a block diagram showing a controller.

One embodiment of the controller 40 is shown in FIG. 4. A DC power supply 42 provides electrical power to the diode laser modules 20. A timer-controlled switch 41 is implemented to automatically turn on and off the power supply 42. An electrical modulation circuit 43 modulates the electrical power to the diode laser modules 20, thereby modulating the output laser power. Such modulation of the laser power is desirable for optimizing the stimulation of an acupuncture point. The timer-controlled switch 41 is used to control the duration of the laser acupuncture therapy, while the laser output modulator 43 the laser power for the procedure.

The above figures and description are intended for illustrating the present invention. It is understood that various modifications can be made without departing from the scopes of the invention as defined in the appended claims.

What is claimed is:

1. A multiple diode laser apparatus for laser acupuncture therapy, comprising:

a set of three or more diode laser modules, each having a diode laser to produce a laser beam at a selected wavelength that has a desired penetration depth into a patient's body part, and having a case for housing said diode laser;

a set of three or more holders respectively coupled to said set of diode laser modules, each configured to hold a diode laser module and having a self-adhesive surface to attach onto said body part to direct a laser beam to an acupuncture point in said body part without holding said respective diode laser module by a user's hand; and a laser controller electrically connected to to provide electrical power to said diode laser modules and to control the output power of said laser beams for the laser acupuncture therapy.

2. An apparatus as in claim 1 wherein a number of said set of three or more diode laser modules ranges from 5 to 10.

3. An apparatus as in claim 1 wherein said selected wavelength is around 635 nm or 830 nm.

4. An apparatus as in claim 1 wherein said output power of said diode laser modules is approximately 5 mW.

5. An apparatus as in claim 1 wherein said diode laser module includes an optical focusing element for modifying said laser beam.

6. An apparatus as in claim 1 wherein said holder has a counterbored hole shaped to tightly hold said diode laser module.

7. An apparatus as in claim 1 wherein said holder is made of a flexible material with a low thermal conductivity.

8. An apparatus as in claim 1 wherein said laser controller comprises a timer operable to automatically turn on and off said electrical power to said diode laser.

9. An apparatus as in claim 1 wherein said diode laser modules each have a length of about 2.5 cm.

10. An apparatus as in claim 1 wherein said diode laser modules have each a weight of about 8 mg.

11. A method for constructing a laser apparatus and performing laser acupuncture therapy, comprising the steps:

providing a set of three or more diode laser modules, each having a diode laser to produce a laser beam at a selected wavelength and having a case for housing said diode laser;

engaging a holder to each diode laser module, said holder having a self-adhesive surface;

attaching each diode laser module onto said body part by said self-adhesive surface in such a way that each diode laser module is attached and positioned at respective acupuncture point without holding by a person's hand; and providing electrical power to said diode laser modules and to control the output power of said laser beams for the laser acupuncture therapy.

12. A method as in claim 11 wherein said laser controller has a timer-controlled switch to control the duration of said laser acupuncture therapy.

13. A method as in claim 11 wherein said laser controller has a modulation circuit to modulate the output power of said laser beam for said laser acupuncture therapy.

* * * * *